(12) United States Patent
Nakano et al.

(10) Patent No.: US 8,367,857 B2
(45) Date of Patent: Feb. 5, 2013

(54) METHOD FOR PRODUCING ISOTHIOCYANATE COMPOUND HAVING CARBOXYL GROUP

(75) Inventors: Satoshi Nakano, Funabashi (JP); Daisuke Saito, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 12/867,339

(22) PCT Filed: Feb. 27, 2009

(86) PCT No.: PCT/JP2009/053729
§ 371 (c)(1),
(2), (4) Date: Aug. 12, 2010

(87) PCT Pub. No.: WO2009/107796
PCT Pub. Date: Sep. 3, 2009

(65) Prior Publication Data
US 2010/0312000 A1    Dec. 9, 2010

(30) Foreign Application Priority Data

Feb. 29, 2008 (JP) .................................. 2008-049369
Oct. 31, 2008 (JP) .................................. 2008-281184

(51) Int. Cl.
*C07C 331/28* (2006.01)
*C07C 331/30* (2006.01)
*C07C 331/20* (2006.01)

(52) U.S. Cl. .......................................... 558/17; 558/18
(58) Field of Classification Search ........................ None
See application file for complete search history.

(56) References Cited

U.S. PATENT DOCUMENTS

| 2,859,235 | A | * | 11/1958 | Schmidt et al. | ................ 558/18 |
| 2,921,953 | A | * | 1/1960 | Kruse et al. | ................ 560/302 |
| 3,341,564 | A | * | 9/1967 | Potts et al. | ................ 558/18 |
| 3,463,853 | A | * | 8/1969 | Ueno et al. | ................ 514/476 |
| 4,064,151 | A | * | 12/1977 | Hedaya et al. | ................ 556/420 |
| 4,228,165 | A |   | 10/1980 | Ogata et al. |  |
| 4,680,338 | A | * | 7/1987 | Sundoro | ................ 525/54.1 |

FOREIGN PATENT DOCUMENTS

| DE | 832891 | * | 7/1949 |
| JP | 54 55550 |   | 5/1979 |
| JP | 54-55550 |   | 5/1979 |
| JP | 7 309831 |   | 11/1995 |
| JP | 9 202767 |   | 8/1997 |
| JP | 10-87605 |   | 4/1998 |
| WO | WO 95/09013 |   | 4/1995 |

OTHER PUBLICATIONS

Kristian et al., "Synthesis and Properties of Aromatic Isothiocyanates Containing Carboxylic Acid Group", Chemical Abstracts, 67:21531, 1967.*

Elbert et al. (Collection Czechoslovak Chem. Commun., vol. 50, 2000-2009, 1985.*

Memeger, W., Jr., "A Novel Synthesis of AB-Aromatic Polyamides from Aromatic Amino Acids and Carbon Disulfide", Polymer Preprints (American Chemical Society, Division of Polymer Chemistry), 17(1), 163-168, 1978.*

Nath, Jayashree et al., "Molecular Iodine Mediated Preparation of Isothiocyanates from Dithiocarbamic Acid Salts", European Journal of Organic Chemistry, 1849-1851, available online Feb. 26, 2009.*

Lago, M. et al. "Preparation of biocides from aspartic acid", Chemical Abstracts, 110:154850, 1989.*

Fry, Harry Shipley, "New Methods of Preparing Thiocarbanilides", Journal of the Americal Chemical Society, 35(10), 1539-1546, 1913.*

Extended European Search Report issued Nov. 9, 2011, in Patent Application No. 09714219.4.

Ulrik Boas, et al., "Facile synthesis of aliphatic isothiocyanates and thioureas on solid phase using peptide coupling reagents", Tetrahedron Letters, vol. 45, XP 002662562, 2004, pp. 269-272.

"The Fifth Series of Experimental Chemistry", Chemical Society of Japan, vol. 14, 2005, pp. 543-551.

D. L. Garmaise, et al., "Amino Acids. VI. Preparation and Chemistry of ω-Carbalkoxyalkyl Isothiocyanates", J. Am. Chem. Soc., vol. 80, 1958, pp. 3332-3334.

Rebecca M. Steele, et al., "Enantioselective cyanosilylation of aldehydes catalysed by a diastereomeric mixture of atropisomeric thioureas", Tetrahedron: Asymmetry, vol. 17, 2006, pp. 999-1006.

Shunji Ito, et al., "Preparation, characterization, and cycloaddition reaction of the heterocumulenes attached directly to azulenes. An efficient strategy for the preparation of azulene-substituted heterocycles", Tetrahedron, vol. 59, 2003, pp. 4651-4659.

F. B. Dains, et al., "Phenyl Isothiocyanate (Isothiocyanic acid, phenyl ester)", Org. Synth., vol. 1, 1941, pp. 447-449.

G. J. M. Van Der Kerk, et al., "ρ-Chlorophenyl Isothiocyanate (Isothiocyanic acid, ρ-chlorophenyl ester)", Org. Synth., vol. 45, 1965, pp. 19-21.

(Continued)

*Primary Examiner* — Fiona T Powers
(74) *Attorney, Agent, or Firm* — Oblon, Spivak, McClelland, Maier & Neustadt, L.L.P.

(57) ABSTRACT

To provide a novel method for producing an isothiocyanate compound having a carboxyl group(s) from the corresponding amino compound having a carboxyl group(s).
A method for producing an isothiocyanate compound which has a carboxyl group(s) and is represented by the formula (2). And the method comprises reacting an amino compound which has a carboxyl group(s) and is represented by the formula (1) (wherein A is e.g. a $C_{6-14}$ aromatic hydrocarbon group or a $C_{1-12}$ saturated hydrocarbon group, and B is e.g. a single bond, a $C_{6-14}$ aromatic hydrocarbon group or a $C_{1-12}$ saturated hydrocarbon group), in a solvent, with carbon disulfide ($CS_2$) and then with a halogen as a simple substance.

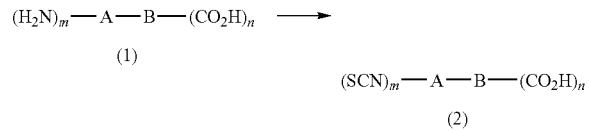

17 Claims, No Drawings

OTHER PUBLICATIONS

Ge Li, et al., "An Improved Procedure for the Preparation of Isothiocyanates from Primary Amines by Using Hydrogen Peroxide as the Dehydrosulfurization Reagent", J. Org. Chem., vol. 62, 1997, pp. 4539-4540.

Tomáš Elbert, et al., "Reaction of 1,6-Anhydro-4-O-Benzyl-2-Deoxy—2-Isothiocyanato-β-D-Glucopyranose; Preparation of 2-Amino-1,6-Anhydro-2,3-Dideoxy-β-D-*ribo*-Hexopyranose", Collection of Czechoslovak Chem. Commun., vol. 50, 1985 pp. 2000-2009.

Rince Wong, et al., "Isothiocyanates from Tosyl Chloride Mediated Decomposition of in Situ Generated Dithiocarbamic Acid Salts", J. Org. Chem., vol. 72, 2007, pp. 2969-2971.

R. L. McKee, et al., "ρ-Substituted Phenyl Isothiocyanates and Some Related Thioureas", J. Am. Chem., vol. 68, 1946, pp. 2506-2507.

Luu Van Boi, et al., "Thiocarbamoylation of amine-containing compounds 1. The reaction of tetramethylthiuram disulfide with 3-amino-4-methylbenzoic acid", Russian Chemical Bulletin, vol. 48, No. 4, Apr. 1999, pp. 739-742.

* cited by examiner

METHOD FOR PRODUCING ISOTHIOCYANATE COMPOUND HAVING CARBOXYL GROUP

TECHNICAL FIELD

The present invention relates to a method for producing an isothiocyanate compound having the carboxyl group(s) from the corresponding amino compound having a carboxyl group(s).

BACKGROUND ART

An isothiocyanate group is a very useful functional group in synthetic organic chemistry since its reactivity is high and it can be led to various chemical structures. And, a carboxyl group is a useful functional group in the field of organic materials, drugs or agricultural chemicals because of its characteristic acidity and hydrogen bonding ability. Accordingly, an isothiocyanate compound having a carboxyl group(s), which has such two functional groups in one molecule, can be said to be a very useful compound as a product or a synthetic intermediate in the field of organic materials, drugs or agricultural chemicals. As an example, it is known that 3,5-diisothiocyanatobenzoic acid is useful as a starting material for the synthesis of a metal-binding polypeptide (e.g. Patent Document 1).

Various methods are known as methods for producing isothiocyanate compounds. Among them, a method for producing an isothiocyanate compound from an amino compound and carbon disulfide is a particularly useful method, since the carbon disulfide to be used is inexpensive, and the atom efficiency is good.

It is generally taken for granted that the method for synthesizing an isothiocyanate from an amino compound and carbon disulfide is suitable for the synthesis of an alkyl isothiocyanate but is inferior in the yield for an aryl isothiocyanate, and that the yield may be improved by using triethylamine as a basic catalyst, but by such a method, it is not possible to synthesize an aryl isothiocyanate having an electron-withdrawing group(s) (e.g. Non-Patent Document 1).

Further, the following methods of employing various additives in the reaction or in the reaction work-up have already been known as methods for synthesizing isothiocyanates. For example, a method of using ethyl chloroformate (Non-Patent Document 2), a method of using dicyclohexylcarbodiimide (Non-Patent Document 3), a method of using phosphorus oxychloride (Non-Patent Document 4), a method of using lead nitrate (Non-Patent Document 5), a method of using acetic anhydride (Patent Document 2), a method of using hydrogen peroxide (Non-Patent Document 6), a method of using sodium chloroacetate and zinc chloride (Non-Patent Document 7), a method of using iodine (Non-Patent Document 8), a method of using tosyl chloride (Non-Patent Document 9), etc. may be mentioned.

While there have been such many reports, there has been no report that an isothiocyanate compound having a carboxyl group(s) was produced by a method of using carbon disulfide and an additive(s) from the corresponding amino compound.

On the other hand, as a method for producing an isothiocyanate compound having the corresponding carboxyl group(s) from the corresponding amino compound, two cases have been reported, i.e. a method of using thiophosgene (Non-Patent Document 10) and a method of using tetramethylthiuram disulfide (Non-Patent Document 11). Among them, the method of using thiophosgene has a problem that thiophosgene itself has a very strong toxicity and bad odor.

Further, the method of employing tetramethylthiuram disulfide has a problem that isolation of reaction intermediate is necessary, whereby the operation is cumbersome; the reaction condition is severe such that heating is carried out at a high temperature in the presence of acid; and tetramethylthiuram disulfide to be used is expensive. Therefore, it has been desired to develop a novel method for producing an isothiocyanate compound having a carboxyl group(s) in a high yield and with high purity without using such reagents, which is useful also as an industrial production method.

Patent Document 1: WO95/09013
Patent Document 2: JP-A-10-87605
Non-Patent Document 1: The Fifth Series of Experimental Chemistry, Vol.14 (2005) p.543-551, compiled by the Chemical Society of Japan.
Non-Patent Document 2: J. Am. Chem. Soc. (1958), 80, 3332
Non-Patent Document 3: Tetrahedron Asymm. (2006), 17, 999
Non-Patent Document 4: Tetrahedron(2003), 59, 4651
Non-Patent Document 5: Org. Synth. (1941), 1, 447
Non-Patent Document 6: Org. Synth. (1965), 45, 19
Non-Patent Document 7: J. Org. Chem. (1997), 62, 4539
Non-Patent Document 8: Collection of Czechoslovak Chem. Commun. (1985), 50, 2000
Non-Patent Document 9: J. Org. Chem. (2007), 72, 3969
Non-Patent Document 10: J. Am. Chem. Soc. (1946), 68, 2506
Non-Patent Document 11: Russ. Chem. Bull. (1999), 48, 739

DISCLOSURE OF THE INVENTION

Object to be Accomplished by the Invention

It is an object of the present invention to provide a novel method for producing an isothiocyanate compound having a carboxyl group(s) from the corresponding amino compound in a high yield and with high purity, which is useful also as an industrial production method.

Means to Accomplish the Object

The present inventors have conducted an extensive study to solve the above problems and as a result, they have found a novel method for producing an isothiocyanate compound having a carboxyl group(s) in a high yield and with high purity and thus accomplished the present invention. That is, the present invention provides the following.

(I) A method for producing an isothiocyanate compound which has a carboxyl group(s) and is represented by the formula (2):

$$(SCN)_m\text{-}A\text{-}B\text{—}(CO_2H)_n \qquad (2)$$

wherein m, n, A and B are, respectively, as defined in the formula (1), said method comprising reacting an amino compound which has a carboxyl group(s) and is represented by the formula (1):

$$(H_2N)_m\text{-}A\text{-}B\text{—}(CO_2H)_n \qquad (1)$$

[wherein each of m and n which are independent of each other, is an integer of 1 or 2, A is a $C_{6-14}$ aromatic hydrocarbon group or a $C_{1-12}$ saturated hydrocarbon group (said $C_{6-14}$ aromatic hydrocarbon group and $C_{1-12}$ saturated hydrocarbon group are unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$ alkylamino group(s), a carboxyl group(s), a $C_{1-6}$ alkylcarbonyl group(s) or a $C_{1-6}$ alkoxycarbonyl group(s), and the methylene group(s) in said $C_{1-12}$ saturated hydrocarbon group may be replaced by an oxygen atom(s), a nitrogen atom(s) substituted by a alkyl group, or a protected nitrogen atom(s)), and B is a single bond, a $C_{6-14}$ aromatic hydrocarbon group or a $C_{1-12}$ saturated hydrocarbon group (said $C_{6-14}$ aromatic hydrocarbon group and $C_{1-12}$ saturated hydrocarbon group are unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di$C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s), and the methylene group(s) in said $C_{1-12}$ saturated hydrocarbon group may be replaced by an oxygen atom(s), a nitrogen atom(s) substituted by a $C_{1-6}$ alkyl group, or a protected nitrogen atom(s))], in a solvent, with carbon disulfide ($CS_2$) and then with a halogen as a simple substance.

(II) The method according to the above (I), wherein A is a $C_{6-14}$ aromatic hydrocarbon group (said $C_{6-14}$ aromatic hydrocarbon group is unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$alkylamino group(s), a $C_{1-6}$ alkylcarbonyl group(s) or a $C_{1-6}$ alkoxycarbonyl group(s)), and B is a single bond or a $C_{1-12}$ saturated hydrocarbon group (said $C_{1-12}$ saturated hydrocarbon group is unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s), and the methylene group(s) in said $C_{1-12}$ saturated hydrocarbon group may be replaced by an oxygen atom(s), a nitrogen atom(s) substituted by a $C_{1-6}$ alkyl group, or a protected nitrogen atom(s)).

(III) The method according to the above (I) or (II), wherein A is a $C_{6-14}$ aromatic hydrocarbon group (said $C_{6-14}$ aromatic hydrocarbon group is unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s)), and B is a single bond or a $C_{1-6}$ alkyl group.

(IV) The method according to any one of the above (I) to (III), wherein A is a $C_{6-14}$ aromatic hydrocarbon group (said $C_{6-14}$ aromatic hydrocarbon group is unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s)), and B is a single bond.

(V) The method according to any one of the above (I) to (IV), wherein A is a $C_{6-14}$ aromatic hydrocarbon group (said $C_{6-14}$ aromatic hydrocarbon group is unsubstituted or substituted by a halogen atom(s), a $C_{1-6}$ alkyl group(s), a hydroxyl group(s) or a $C_{1-6}$ alkoxy group(s)).

(VI) The method according to the above (I), wherein A is a $C_{1-12}$ saturated hydrocarbon group (said $C_{1-2}$ saturated hydrocarbon group is unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$ alkylamino group(s), a carboxyl group(s), a $C_{1-6}$ alkylcarbonyl group(s) or a $C_{1-6}$ alkoxycarbonyl group(s), and the methylene group(s) in said $C_{1-12}$ saturated hydrocarbon group may be replaced by an oxygen atom(s), a nitrogen atom(s) substituted by a $C_{1-6}$ alkyl group, or a protected nitrogen atom(s)), and B is a single bond or a $C_{6-14}$ aromatic hydrocarbon group (said $C_{6-14}$ aromatic hydrocarbon group is unsubstituted or substituted by a halogen atom(s), a nitro group(s), a cyano group(s), a $C_{1-6}$ alkyl group(s), a hydroxyl group(s), a protected hydroxyl group(s), a $C_{1-6}$ alkoxy group(s), a di $C_{1-6}$ alkylamino group(s), a protected amino group(s), a protected mono $C_{1-6}$ alkylamino group(s), a $C_{1-6}$ alkylcarbonyl group(s) or a $C_{1-6}$ alkoxycarbonyl group(s)).

(VII) The method according to the above (VI), wherein A is a $C_{1-12}$ saturated hydrocarbon group, and B is a single bond or a $C_{6-14}$ aromatic hydrocarbon group (said $C_{6-14}$ aromatic hydrocarbon group is unsubstituted or substituted by a halogen atom(s), a $C_{1-6}$ alkyl group(s), a hydroxyl group(s) or a $C_{1-6}$ alkoxy group(s)).

(VIII) The method according to the above (VII), wherein A is a $C_{1-12}$ saturated hydrocarbon group, and B is a single bond or a $C_{6-14}$ aromatic hydrocarbon group.

(IX) The method according to the above (VIII), wherein A is a $C_{1-12}$ saturated hydrocarbon group, and B is a single bond.

(X) The method according to the above (VIII), wherein A is a $C_{1-6}$ saturated hydrocarbon group, and B is a phenyl group.

(XI) The method according to any one of the above (I) to (X), wherein m is 1.

(XII) The method according to any one of the above (I) to (XI), wherein n is 1.

(XIII) The method according to any the above (I) to (X) and (XII), wherein m is 2.

(XIV) The method according to any one of the above (I) to (XI) and (XIII), wherein n is 2.

(XV) The method according to any one of the above (I) to (XIV), wherein the reaction of the amino compound having a carboxyl group(s) with carbon disulfide is carried out in the presence of a base.

(XVI) The method according to the above (XV), wherein the base is an organic amine or an inorganic base.

(XVII) The method according to any one of the above (I) to (XV), wherein the halogen as a simple substance is iodine.

Advantageous Effects of the Invention

According to the present invention, it is possible to provide a novel method whereby without using strongly toxic thiophosgene or expensive tetramethylthiuram disulfide, the corresponding isothiocyanate compound can be produced safely, inexpensively, simply in a high yield and with high purity under mild conditions.

BEST MODE FOR CARRYING OUT THE INVENTION

Now, the present invention will be described in further detail.

In the present invention, "n" means normal, "i" iso, "s" secondary, "t" tertiary, "c" cyclo, "o" ortho, "m" meta, "p" para, and "Me" a methyl group.

The $C_{1-12}$ saturated hydrocarbon group represents a bivalent or trivalent group derived from a linear, branched or cyclic saturated hydrocarbon having from 1 to 12 carbon atoms and may, for example, be a bivalent or trivalent group derived from e.g. methane, ethane, n-propane, n-butane, n-pentane, n-hexane, n-heptane, n-octane, i-propane, i-butane, t-butane, s-butane, i-pentane, neopentane, t-pentane, c-propane, c-butane, c-pentane, c-hexane, c-heptane, c-hexylmethane or c-hexylethane.

The $C_{1-12}$ saturated hydrocarbon group in A and B in the formula (1) may have a substituent as defined in the definition of A or B. For example, the $C_{1-12}$ saturated hydrocarbon group for A when m is 1, or the $C_{1-12}$ saturated hydrocarbon group for B when n is 1, is a linear, branched or cyclic alkylene (alkane-diyl) group having from 1 to 12 carbon atoms, and such an alkylene group is unsubstituted or substituted as defined in the definition of A or B.

Further, the $C_{1-12}$ saturated hydrocarbon group for A when m is 2, or the $C_{1-12}$ saturated hydrocarbon group for B when n is 2, is a linear, branched or cyclic alkane-triyl group having from 1 to 12 carbon atoms, and such an alkane-triyl group is unsubstituted or substituted as defined in the definition of A or B.

The $C_{1-6}$ saturated hydrocarbon group represents a bivalent or trivalent group derived from a linear, branched or cyclic saturated hydrocarbon having from 1 to 6 carbon atoms in the above-described $C_{1-12}$ saturated hydrocarbon group and may, for example, be a bivalent or trivalent group derived from e.g. methane, ethane, n-propane, n-butane, n-pentane, n-hexane, i-propane, i-butane, t-butane, s-butane, i-pentane, neopentane, t-pentane, c-propane, c-butane, c-pentane or c-hexane.

The $C_{1-6}$ alkyl group represents a linear, branched or cyclic alkyl group having from 1 to 6 carbon atoms and may, for example, be a methyl group, an ethyl group, a n-propyl group, a n-butyl group, a n-pentyl group, a n-hexyl group, an i-propyl group, an i-butyl group, a t-butyl group, a s-butyl group, an i-pentyl group, a neopentyl group, a t-pentyl group, a c-propyl group, a c-butyl group, a c-pentyl group or a c-hexyl group.

The $C_{1-6}$ alkoxy group represents a linear or branched alkoxy group having from 1 to 6 carbon atoms and may, for example, be a methoxy group, an ethoxy group, a n-propoxy group, an i-propoxy group, a n-butoxy group, an i-butoxy group, a s-butoxy group, a t-butoxy group, a n-pentyloxy group, an i-pentyloxy group, a n-hexyloxy group, a c-butyloxy group, a c-pentyloxy group or a c-hexyloxy group.

The $C_{1-6}$ alkylcarbonyl group represents a carbonyl group substituted by a $C_{1-6}$ alkyl group and may, for example, be a methylcarbonyl group, an ethylcarbonyl group, a n-propylcarbonyl group, a n-butylcarbonyl group, a n-pentylcarbonyl group, a n-hexylcarbonyl group, an i-propylcarbonyl group, an i-butylcarbonyl group, a t-butylcarbonyl group, a s-butylcarbonyl group, an i-pentylcarbonyl group, a neopentylcarbonyl group, a t-pentylcarbonyl group, a c-propylcarbonyl group, a c-butylcarbonyl group, a c-pentylcarbonyl group or a c-hexylcarbonyl group.

The mono $C_{1-6}$ alkylamino group represents an amino group substituted by one $C_{1-6}$ alkyl group and may, for example, be an N-methylamino group, an N-ethylamino group, an N-n-propylamino group, an N-i-propylamino group, an N-n-butylamino group, an N-i-butylamino group, an N-s-butylamino group, an N-t-butylamino group, an N-n-pentylamino group, an N-i-pentylamino group, an N-neopentylamino group, an N-t-pentylamino group, an N-n-hexylamino group, an N-c-propylamino group, an N-c-butylamino group, an N-c-pentylamino group, an N-c-hexylamino group, an N-c-propylmethylamino group, an N-c-butylmethylamino group or an N-c-pentylmethylamino group.

The di $C_{1-6}$ alkylamino group represents an amino group substituted by the same or different two $C_{1-6}$ alkyl groups and may, for example, be an N,N-dimethylamino group, an N,N-diethylamino group, an N,N-di-n-propylamino group, an N,N-di-i-propylamino group, an N-methyl-N-ethylamino group, an N-methyl-N-n-propylamino group, an N-methyl-N-i-propylamino group, an N-ethyl-N-n-propylamino group, an N-ethyl-N-i-propylamino group or an N-n-propyl-N-i-propylamino group.

The $C_{1-6}$ alkoxycarbonyl group represents a carbonyl group substituted by a $C_{1-6}$ alkoxy group and may, for example, be a methoxycarbonyl group, an ethoxycarbonyl group, a n-propoxycarbonyl group, an i-propoxycarbonyl group, a n-butoxycarbonyl group, an i-butoxycarbonyl group, a s-butoxycarbonyl group, a t-butoxycarbonyl group, a n-pentyloxycarbonyl group, an i-pentyloxycarbonyl group, a n-hexyloxycarbonyl group, a c-butyloxycarbonyl group, a c-pentyloxycarbonyl group or a c-hexyloxycarbonyl group.

The $C_{6-14}$ aromatic hydrocarbon group is an aromatic hydrocarbon group having from 6 to 14 carbon atoms and may, for example, be a bivalent or trivalent group derived from benzene, naphthalene, biphenyl or anthracene.

The $C_{6-14}$ aromatic hydrocarbon group in A and B in the formula (1), may be substituted as defined in the definition of A or B. For example, the $C_{6-14}$ aromatic hydrocarbon group for A when m is 1, or the $C_{6-14}$ aromatic hydrocarbon group for B when n is 1, is an arylene(aryl-diyl) group having from 6 to 14 carbon atoms, and such arylene group is unsubstituted or substituted as defined in the definition of A or B.

Further, the $C_{6-14}$ aromatic hydrocarbon group for A when m is 2, or the $C_{6-14}$ aromatic hydrocarbon group for B when n is 2, is a linear, branched or cyclic aryl-triyl group having from 6 to 14 carbon atoms, and such an aryl-triyl group is unsubstituted or substituted as defined in the definition of A or B.

In the present invention, "protected" in e.g. the protected hydroxyl group, the protected amino group, the protected mono $C_{1-6}$ alkylamino group and the protected nitrogen atom means that a highly reactive functional group such as a hydroxyl group or an amino group is substituted to be an inert functional group under the reaction condition with carbon disulfide and a halogen as a simple substance in the present invention.

The protecting group in the protected hydroxyl group may be any protecting group so long as it is effective as a protecting group for a hydroxyl group, and for example, protecting groups disclosed in Greene's Protective Groups in Organic Synthesis (4th ed.), John Wiley, 2007, pp. 24-299 may be mentioned. Preferred as protecting groups for a hydroxyl group may, for example, be a methoxymethyl group, an acetyl group, a benzyl group, a trimethylsilyl group, etc.

The protecting groups in the protected amino group, the protected mono $C_{1-6}$ alkylamino group and the protected nitrogen atom may be any protecting groups so long as they are effective as protecting groups for a nitrogen atom, but, for example, protecting groups disclosed in e.g. Greene's Protective Groups in Organic Synthesis (4th ed.), John Wiley, 2007, pp. 706-872 may be mentioned. Preferred as such protecting groups may, for example, be an acetyl group, t-butoxycarbonyl group, etc.

In the present invention, the halogen atom is a fluorine atom, a chlorine atom, a bromine atom or an iodine atom. The halogen as a simple substance is fluorine, chlorine, bromine or iodine. The halogen as a simple substance to be used for the reaction of the present invention is preferably bromine or iodine, more preferably iodine.

In the present invention, the $C_{6-14}$ aromatic hydrocarbon group is preferably a phenylene group or a naphthylene group, particularly preferably a phenylene group. Further, the substituent for the $C_{6-14}$ aromatic hydrocarbon group in A is as mentioned above, and is more preferably a halogen atom, a $C_{1-3}$ alkyl group, a hydroxyl group or a $C_{1-3}$ alkoxy group, further preferably a chlorine atom, a hydroxyl group, a methyl group or a methoxy group.

The $C_{1-12}$ saturated hydrocarbon group in A is preferably a $C_{1-6}$ saturated hydrocarbon group, more preferably a $C_{1-3}$ saturated hydrocarbon group.

In the method of the present invention, firstly, an amino compound having a carboxyl group(s) as a raw material, is reacted, in a solvent for the reaction, with carbon disulfide ($CS_2$) and then with a halogen as a simple substance.

The solvent to be used for the method of the present invention is not particularly limited so long as it is a solvent which is stable under the reaction conditions and inert to the reaction not to prevent the reaction. However, the raw material of the present invention is an amino compound having a carboxyl group(s), which is a so-called amphoteric compound, and under a basic reaction condition, the carboxyl group forms a salt. Therefore, the solvent is preferably one wherein these raw material compounds are soluble.

As such a solvent, it is preferred to employ water, an organic solvent or a mixed solvent of water and a water-soluble organic solvent. Specific examples of the organic solvent include acetonitrile, N,N-dimethylformamide, acetone, chloroform, dichloromethane, etc. Further, a specific example of the above-mentioned mixed solvent of water and a water-soluble organic solvent may be a mixed solvent of water and at least one water-soluble organic solvent selecting from the group consisting of tetrahydrofuran, 1,4-dioxane, N,N-dimethylformamide, ethanol, i-propanol, acetone and dimethylsulfoxide. A preferred solvent is a mixed solvent of water and tetrahydrofuran, or acetonitrile. The amount of the solvent to be used is preferably from 1 to 20 times by volume, preferably from 6 to 15 times by volume, to the amino compound having a carboxyl group(s), and in the case of the mixed solvent of water and a water soluble organic solvent, the volume ratio of the water/the water-soluble organic solvent is preferably from 2:1 to 1:10, particularly preferably from 1:1 to 1:2.

Further, in a case where iodine is used as the after-mentioned halogen as a simple substance, it is preferred to use, as the solvent, water, an organic solvent or a mixed solvent of water and a water-soluble organic solvent. Further, in a case where bromine or chlorine is used as the halogen as a simple substance, it is preferred to use, as the solvent, an organic solvent. A specific example of such an organic solvent may be N,N-dimethylformamide or acetonitrile, preferably N,N-dimethylformamide.

The amount of carbon disulfide to be used in the method of the present invention is, per one mole of the amino compound having a carboxyl group(s) as the raw material, from (the number of amino groups in one molecule of the raw material * 1.0) mol to (the number of amino groups in one molecule of the raw material×10.0) mol, preferably from (the number of amino groups in one molecule of the raw material×2.0) mol to (the number of amino groups in one molecule of the raw material×4.0) mol.

In the method of the present invention, it is possible to add and react the amino compound having a carboxyl group(s) as the raw material, with carbon disulfide and the halogen, at the same time. However, it is preferred that the raw material is reacted with carbon disulfide and then, the halogen as a simple substance is reacted thereto.

The amount of the halogen as a simple substance to be used in the method of the present invention is, per one mole of the amino compound having a carboxyl group(s) as the raw material, from (the number of amino groups in one molecule of the raw material×1.0) mol to (the number of amino groups in one molecule of the raw material×2.0) mol, preferably from (the number of amino groups in one molecule of the raw material× 1.0) mol to (the number of amino groups in one molecule of the raw material×1.2) mol.

The reaction with carbon disulfide in the present invention is preferably carried out in the presence of a base.

Such a base may, for example, be an organic amine such as diethylamine, triethylamine, diisopropylethylamine, tri-n-propylamine, tri-n-butylamine, DBN (1,5-diazabicyclo[4.3.0]-5-nonene), DBU (1,8-diazabicyclo[5.4.0]-7-undecene), N-methylmorpholine or N,N-dimethylaniline; or an inorganic base such as sodium hydroxide, potassium carbonate or sodium hydrogencarbonate. Among them, preferred is an organic amine; more preferred is a trialkylamine such as triethylamine, diisopropylethylamine, tri-n-propylamine or tri-n-butylamine; and particularly preferred is triethylamine. The amount of the base to be used is, per one mole of the amino compound having a carboxyl group(s) as the raw material, [from (the number of carboxyl groups in one molecule of the raw material×1.0+the number of amino groups in one molecule of the raw material×1.0) mol to (the number of carboxyl groups in one molecule of the raw material×1.0+the number of amino groups in one molecule of the raw material× 5.0)] mol, preferably [from (the number of carboxyl groups in one molecule of the raw material×1.0 +the number of amino groups in one molecule of the raw material×1.5) mol to (the number of carboxyl groups in one molecule of the raw material×1.0 +the number of amino groups in one molecule of the raw material×2.5)] mol.

The reaction in the method of the present invention can be carried out at a temperature within a range of from a temperature at which the solvent does not freeze to the boiling point of the solvent. In a case where water or a mixed solvent of water and a water-soluble organic solvent, is used as the solvent, the reaction temperature is preferably from 0 to 40° C. Especially when the amino compound having a carboxyl group(s) is reacted with carbon disulfide and a base, the temperature is preferably from 20 to 30° C., and when the material is then reacted with a halogen as a simple substance, the temperature is preferably from 0 to 10° C. If the reaction temperature is lower than the above range, stirring tends to be difficult, and if it is higher than the above range, a side reaction is likely to proceed. In the method of the present invention, in a case where an organic solvent is used as the solvent, a preferred reaction temperature is within a range of from –10 to 40° C., and especially when the amino compound having a carboxyl group(s) is reacted with carbon disulfide and a base, the temperature is preferably from 20 to 30° C., and when the material is then reacted with a halogen as a simple substance, the temperature is preferably from ×10to 10° C.

In the present invention, the reaction times for reacting the amino compound having a carboxyl group(s) as the raw material with carbon disulfide and then reacting a halogen as a simple substance, vary depending upon the reaction temperatures, the type and amount of the raw material and may suitably be changed depending upon the respective conditions. A preferred reaction time for reacting the amino compound having a carboxyl group as the raw material with carbon disulfide is from 3 to 72 hours, more preferably from 6 to 44 hours. The reaction time for reacting the halogen as a simple substance is from 0.5 to 5 hours, preferably from 1.5 to 2.5 hours.

In the present invention, the reaction of the amino compound having a carboxyl group(s) as the raw material with carbon disulfide, and further, the subsequent reaction with the halogen as a simple substance, may each be carried out in the presence of air. That is, the reaction can simply be carried out without necessity to replace the interior atmosphere of the reactor with nitrogen.

In the foregoing, the present invention has been described with reference to cases where an amino compound having a carboxyl group being a pure raw material is used. However, in a case where such a raw material contains an isomer such as a tautomer, a geometrical isomer or an optical isomer, the present invention includes a method of employing such an isomer or a mixture of isomers.

EXAMPLES

Now, the present invention will be described in further detail with reference to Examples. However, it should be understood that the present invention is by no means thereby restricted. In Examples, NMR means nuclear magnetic resonance, HPLC means high performance liquid chromatography, LC-MS means liquid chromatography-mass spectrometry, ES means electrospray, and v means volume. Further, HPLC purity means the area percentage unless otherwise specified.

Further, measuring conditions for various measurements are as follows.

Measuring Condition for LC-MS (Condition 1)

Equipment used: alliance-ZQ LC-MS SYSTEM, manufactured by Waters
Column used: SunFire C18 ((average particle diameter of filler: 3.5 μm), 2.1 mm I.D.×20 mm (inner diameter of column×length of column), the same applies hereinafter)
Column temperature: 40° C.
Solvent composition:
0 min. acetonitrile/0.2 vol % formic acid aqueous solution 10/90 (v/v)
3.0 min. acetonitrile/0.2 vol % formic acid aqueous solution 85/15 (v/v)
5.0 min. acetonitrile/0.2 vol % formic acid aqueous solution 85/15 (v/v)
5.5 min. acetonitrile/0.2 vol % formic acid aqueous solution 95/5 (v/v)
7.0 min. acetonitrile/0.2 vol % formic acid aqueous solution 95/5 (v/v)
Flow rate: 0.4 mL/min Measuring Condition for LC-MS (Condition 2)

Equipment used: alliance-ZQ LC-MS SYSTEM, manufactured by Waters
Column used: Xterra MS C18 ((3.5 μm), 2.1 mm I.D.×20 mm)
Column temperature: 40° C.
Solvent composition:
0 min. acetonitrile/0.2 vol % formic acid aqueous solution 20/80 (v/v)
0.5 min. acetonitrile/0.2 vol % formic acid aqueous solution 20/80 (v/v)
3.5 min. acetonitrile/0.2 vol % formic acid aqueous solution 90/10 (v/v)
7.0 min. acetonitrile/0.2 vol % formic acid aqueous solution 90/10 (v/v)
Flow rate: 0.4 mL/min Measuring Condition for LC-MS (Condition 3)

Equipment used: 1100MSD-Trap, manufactured by Agilent
Column used: Atlantis dC18 ((5 μm), 2.1 mm I.D.×150 mm)
Column temperature: 40° C.
Solvent composition:
0 min. acetonitrile/0.1 vol % formic acid aqueous solution 10/90 (v/v)
5.0 min. acetonitrile/0.1 vol % formic acid aqueous solution 10/90 (v/v)
20.0 min. acetonitrile/0.1 vol % formic acid aqueous solution 90/10 (v/v)
40.0 min. acetonitrile/0.1 vol % formic acid aqueous solution 90/10 (v/v)
Flow rate: 0.2 mL/min Measuring Condition for HPLC Equipment used: SHIMADZU LC-10A series, manufactured by Shimadzu Corporation
Column used: INERTSIL ODS 2 ((5 μm), 4.6 mm I.D.×250 mm)
Column temperature: 40° C.
Detection: UV 254 nm
Solvent composition:
0 min. acetonitrile/20 mM phosphoric acid aqueous solution 80/20 (v/v)
40.0 min. acetonitrile/20 mM phosphoric acid aqueous solution 80/20 (v/v)
Flow rate: 1.0mL/min
A $^1$H-NMR spectrum was measured by using JNM-ECP300 and JNM-ECX300 manufactured by JEOL Ltd., at 300 MHz in deuterated chloroform (CDCl3).

Example 1

4-Isothiocyanatobenzoic acid
Carbon disulfide (0.66 mL, 11 mmol) was added to a mixture comprising 4-aminobenzoic acid (0.50 g, 3.6 mmol), tetrahydrofuran (2.5 mL), water (2.5 mL) and triethylamine (1.3 mL, 9.1 mmol), followed by stirring at room temperature for 24 hours. To the obtained reaction mixture, a tetrahydrofuran (2.5 mL) solution of iodine (1.0 g, 4.0 mmol) was dropwise added over a period of 5 minutes at 0° C., followed by stirring at 0° C. for further two hours. Thereafter, 1M hydrochloric acid (3.6 mL) and sodium sulfite (91 mg, 0.72 mmol) were added and stirred. Then, ethyl acetate (15 mL) was added, and the organic layer was separated and concentrated under reduced pressure to dryness. To the residue, ethyl acetate (5 mL) and hexane (5 mL) were added and thoroughly mixed, and then, the insoluble matter was collected by filtration to obtain 4-isothiocyanatobenzoic acid as a colorless solid (0.65 g, yield: 100%, HPLC purity: 92%, HPLC retention time: 3.7 min). LC-MS ES-178 (retention time: 4.0 min, condition 1).

Comparative Example 1

4-Isothiocyanatobenzoic acid
The production method disclosed in Collection of Czechoslovak Chem. Commun. 50, 2000 (1985), was applied to 4-aminobenzoic acid (an amino compound having a carboxyl group), but both the yield and the purity were low, as shown below.
A mixture comprising 4-aminobenzoic acid (0.20 g, 1.5 mmol), dioxane (5 mL), a saturated sodium hydrogencarbonate aqueous solution (5 mL) and carbon disulfide (0.37 mL, 6.1 mmol) was stirred in a nitrogen atmosphere at room temperature for 19 hours and then concentrated under reduced pressure to dryness. The obtained residue was dissolved in water (8.0 mL), and 1M sodium hydroxide aqueous solution (1.5 mL) was added. With stirring at room temperature, an ethanol (8.0 mL) solution of iodine (0.38 g, 1.5 mmol) was dropwise added thereto over a period of 8 minutes, followed by stirring at room temperature for further 12 minutes. Then, the insoluble matter was removed by filtration. The filtrate was concentrated under reduced pressure to remove ethanol and dioxane as far as possible. Then, 1M hydrochloric acid (4.5 mL) was added, and the precipitated solid was collected by filtration to obtain 4-isothiocyanatobenzoic acid as a ocher solid (0.20 g, yield: 78%). The HPLC purity was 62%.

Example 2

3-Isothiocyanatobenzoic acid

Carbon disulfide (0.26 mL, 4.4 mmol) was added to a mixture comprising 3-aminobenzoic acid (0.20 g, 1.5 mmol), tetrahydrofuran (1.0 mL), water (1.0 mL) and triethylamine (0.51 mL, 3.6 mmol), followed by stirring at room temperature for 24 hours. To the obtained reaction mixture, a tetrahydrofuran (1.0 mL) solution of iodine (0.41 g, 1.6 mmol) was dropwise added over a period of 5 minutes at 0° C., followed by stirring at 0° C. for further two hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the residue, ethyl acetate (4 mL) and water (2 mL) were added, and the organic layer was concentrated under reduced pressure to dryness to obtain 3-isothiocyanatobenzoic acid as a cream-colored solid (0.25 g, yield: 96%, HPLC purity: 95%, HPLC retention time: 3.6 min). LC-MS ES-178 (retention time: 4.0 min, condition 1).

Example 3

4-Isothiocyanato-2-chlorobenzoic acid

Carbon disulfide (0.26 mL, 4.4 mmol) was added to a mixture comprising 4-amino-2-chlorobenzoic acid (0.26 g, 1.5 mmol), tetrahydrofuran (1.0 mL), water (1.0 mL) and triethylamine (0.51 mL, 3.6 mmol), followed by stirring at room temperature for 24.5 hours. To the obtained reaction mixture, a tetrahydrofuran (1.0 mL) solution of iodine (0.41 g, 1.6 mmol) was dropwise added over a period of 5 minutes at 0° C., followed by stirring at 0° C. for further two hours. Thereafter, 1M hydrochloric acid (1.5 mL) and sodium sulfite (38 mg, 0.30 mmol) were added and stirred. Then, ethyl acetate (6 mL) was added, and the organic layer was separated and concentrated under reduced pressure to dryness. To the residue, water (4 mL) and sodium hydrogencarbonate (0.14 g, 1.7 mmol) were added, and the insoluble matter was removed by filtration. To the filtrate, 1M hydrochloric acid (1.5 mL) and water (2.0 mL) were added, and the precipitated solid was collected by filtration. To this solid, ethyl acetate (6 mL), water (2.0 mL) and sodium hydrogencarbonate (25 mg, 1.7 mmol) were added, and the organic layer was concentrated under reduced pressure to dryness to obtain 4-isothiocyanato-2-chlorobenzoic acid as a white solid (0.20 g, yield: 62%, HPLC purity: 91%, HPLC retention time: 3.9 min). LC-MS ES-212, 214 (retention time: 4.2 min, condition 1).

Example 4

4-Isothiocyanato-3-methylbenzoic acid

Carbon disulfide (0.26 mL, 4.4 mmol) was added to a mixture comprising 4-amino-3-methylbenzoic acid (0.23 g, 1.5 mmol), tetrahydrofuran (1.0 mL), water (1.0 mL) and triethylamine (0.51 mL, 3.6 mmol), followed by stirring at room temperature for 28 hours. The obtained reaction mixture was dropwise added to a tetrahydrofuran (1.0 mL) solution of iodine (0.41 g, 1.6 mmol) over a period of 5 minutes at 0° C., followed by stirring at 0° C. for further 1.5 hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the residue, ethyl acetate (6 mL) and water (1 mL) were added, and the organic layer was washed once with 1M hydrochloric acid (1 mL) and then concentrated under reduced pressure to dryness to obtain 4-isothiocyanato-3-methylbenzoic acid as a cream-colored solid (0.30 g, yield: 103%, HPLC purity: 88%, HPLC retention time: 4.0 min). LC-MS ES-192 (retention time: 4.3 min, condition 1).

Example 5

3-Isothiocyanato-4-methylbenzoic acid

Carbon disulfide (0.26 mL, 4.4 mmol) was added to a mixture comprising 3-amino-4-methylbenzoic acid (0.23 g, 1.5 mmol), tetrahydrofuran (1.0 mL), water (1.0 mL) and triethylamine (0.51 mL, 3.6 mmol), followed by stirring at room temperature for 26 hours. The obtained reaction mixture was dropwise added to a tetrahydrofuran (1.0 mL) solution of iodine (0.41 g, 1.6 mmol) over a period of two minutes at 0° C., followed by stirring at 0° C. for further two hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the residue, ethyl acetate (6 mL) and water (1 mL) were added, and the organic layer was concentrated under reduced pressure to dryness to obtain 3-isothiocyanato-4-methylbenzoic acid as a ocher solid (0.26 g, yield: 91%, HPLC purity: 95%, HPLC retention time: 3.9 min). LC-MS ES-192 (retention time: 4.3 min, condition 1).

Example 6

4-Isothiocyanato-2-hydroxybenzoic acid

Carbon disulfide (0.26 mL, 4.4 mmol) was added to a mixture comprising 4-amino-2-hydroxybenzoic acid (0.23 g, 1.5 mmol), tetrahydrofuran (1.0 mL), water (1.0 mL) and triethylamine (0.51 mL, 3.6 mmol), followed by stirring at room temperature for 31 hours. To the obtained reaction mixture, a tetrahydrofuran (1.0 mL) solution of iodine (0.41 g, 1.6 mmol) was dropwise added over a period of 3 minutes at 0° C., followed by stirring at 0° C. for further 2.5 hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the obtained residue, ethyl acetate (6 mL), water (2 mL) and sodium hydrogencarbonate (13 mg, 0.15 mmol) were added, and the organic layer was washed twice with water (2 mL) and then concentrated under reduced pressure to dryness. To the obtained residue, chloroform (1 mL) and hexane (3 mL) were added and thoroughly mixed, and then, an insoluble matter was removed by filtration. The filtrate was concentrated under reduced pressure to dryness to obtain 4-isothiocyanato-2-hydroxybenzoic acid as a brown-colored solid (0.18 g, yield: 64%, HPLC purity: 86%, HPLC retention time: 4.6 min). LC-MS ES-194 (retention time: 4.4 min, condition 1).

Example 7

5-Isothiocyanato-2-hydroxybenzoic acid

Carbon disulfide (0.26 mL, 4.4 mmol) was added to a mixture comprising 5-amino-2-hydroxybenzoic acid (0.23 g, 1.5 mmol), tetrahydrofuran (1.0 mL), water (1.0 mL) and triethylamine (0.51 mL, 3.6 mmol), followed by stirring at room temperature for 17 hours. The obtained reaction mixture was dropwise added to a tetrahydrofuran (1.0 mL) solution of iodine (0.41 g, 1.6 mmol) over a period of 5 minutes at 0° C., followed by stirring at 0° C. for further 2.5 hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the residue, ethyl acetate (6 mL) and water (1 mL) were added, and the organic layer was concentrated under reduced pressure to dryness to obtain 5-isothiocyanato-2-hydroxybenzoic acid as a gray solid (0.29 g, yield: 100%, HPLC purity: 97%, HPLC retention time: 4.3 min). LC-MS ES-194 (retention time: 4.4 min, condition 1).

Example 8

3-Isothiocyanato-4-methoxybenzoic acid

Carbon disulfide (0.26 mL, 4.4 mmol) was added to a mixture comprising 3-amino-4-methoxybenzoic acid (0.25 g, 1.5 mmol), tetrahydrofuran (1.0 mL), water (1.0 mL) and triethylamine (0.51 mL, 3.6 mmol), followed by stirring at room temperature for 6 hours. To the obtained reaction mixture, a tetrahydrofuran (1.0 mL) solution of iodine (0.41 g, 1.6 mmol) was dropwise added over a period of 5 minutes at 0° C., followed by stirring at 0° C. for further 2.5 hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the obtained residue, ethyl acetate (6 mL), water (2 mL), sodium hydrogencarbonate (6 mg, 0.07 mmol) and sodium sulfite (9 mg, 0.07 mmol) were added, the organic layer was separated and concentrated under reduced pressure to dryness to obtain 3-isothiocyanato-4-methoxybenzoic acid as a colorless solid (0.29 g, yield: 94%, HPLC purity: 99%, HPLC retention time: 3.5 min). LC-MS ES-208 (retention time: 21.6 min, condition 3).

Example 9

6-Isothiocyanato-2-naphthoic acid

Carbon disulfide (0.26 mL, 4.4 mmol) was added to a mixture comprising 6-amino-2-naphthoic acid (0.28 g, 1.5 mmol), tetrahydrofuran (1.0 mL), water (1.0 mL) and triethylamine (0.51 mL, 3.6 mmol), followed by stirring at room temperature for 24 hours. To the obtained reaction mixture, a tetrahydrofuran (1.0 mL) solution of iodine (0.41 g, 1.6 mmol) was dropwise added over a period of 5 minutes at 0° C., followed by stirring at 0° C. for further two hours. Thereafter, 1M hydrochloric acid (1.5 mL) and sodium sulfite (38 mg, 0.30 mmol) were added and mixed. The formed insoluble matter was collected by filtration and dried under reduced pressure. Then, carbon disulfide (2.0 mL) was added and thoroughly mixed. Then, the insoluble matter was collected by filtration to obtain 6-isothiocyanato-2-naphthoic acid as a cream-colored solid (0.32 g, yield: 96%, HPLC purity: 94%, HPLC retention time: 3.7 min). LC-MS ES-228 (retention time: 4.5 min, condition 1).

Example 10

3,5-Diisothiocyanatobenzoic acid

Carbon disulfide (0.54 mL, 9.1 mmol) was added to a mixture comprising 3,5-diaminobenzoic acid (0.23 g, 1.5 mmol), tetrahydrofuran (1.0 mL), water (1.0 mL) and triethylamine (0.84 mL, 6.0 mmol), followed by stirring at room temperature for 31 hours. To the obtained reaction mixture, a tetrahydrofuran (2.0 mL) solution of iodine (0.82 g, 1.6 mmol) was dropwise added over a period of 5 minutes at 0° C., followed by stirring at 0° C. for further 2.5 hours. Thereafter, 1M hydrochloric acid (1.5 mL) and sodium sulfite (76 mg, 0.30 mmol) were added and mixed. Then, ethyl acetate (6 mL) was added, and the organic layer was separated and concentrated under reduced pressure to dryness. To the obtained residue, ethyl acetate (6 mL), water (3 mL) and sodium hydrogencarbonate (10 mg, 0.12 mmol) were added, and the organic layer was concentrated under reduced pressure to dryness. To the obtained residue, chloroform (6 mL) was added and thoroughly mixed, and then an insoluble matter was removed by filtration. The filtrate was concentrated under reduced pressure to dryness, and then, to the obtained residue, chloroform (6 mL) and hexane (1 mL) were added and thoroughly mixed. Then, the insoluble matter was removed by filtration. The filtrate was concentrated under reduced pressure to dryness to obtain 3,5-diisothiocyanatobenzoic acid as a colorless solid (0.31 g, yield: 86%, HPLC purity: 97%, HPLC retention time: 5.3 min). LC-MS ES-235 (retention time: 4.6 min, condition 1).

Example 11

5-Isothiocyanatoisophthalic acid

Carbon disulfide (0.26 mL, 4.4 mmol) was added to a mixture comprising 5-aminoisophthalic acid (0.30 g, 1.5 mmol), tetrahydrofuran (1.0 mL), water (1.0 mL) and triethylamine (0.51 mL, 3.6 mmol), followed by stirring at room temperature for 61hours. The obtained reaction mixture was dropwise added to a tetrahydrofuran (1.0 mL) solution of iodine (0.41 g, 1.6 mmol) over a period of 5 minutes at 0° C., followed by stirring at 0° C. for further two hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the residue, ethyl acetate (5 mL) was added and thoroughly mixed. Then, the insoluble matter was filtered off. The filtrate was concentrated under reduced pressure to dryness to obtain 5-isothiocyanatoisophthalic acid as a cream-colored solid (0.33 g, yield: 100%, HPLC purity: 88%, HPLC retention time: 2.8min). LC-MS ES-222 (retention time: 3.7 min, condition 1).

Example 12

2-(4-Isothiocyanatophenyl)acetic acid

Carbon disulfide (0.26 mL, 4.4 mmol) was added to a mixture comprising 2-(4-aminophenyl)acetic acid (0.23 g, 1.5 mmol), tetrahydrofuran (1.0 mL), water (1.0 mL) and triethylamine (0.51 mL, 3.6 mmol), followed by stirring at room temperature for 24 hours. To the obtained reaction mixture, a tetrahydrofuran (1.0 mL) solution of iodine (0.41 g, 1.6 mmol) was dropwise added over a period of 8 minutes at 0° C., followed by stirring at 0° C. for further 1.5 hours. Thereafter, 1M hydrochloric acid (1.5 mL) and sodium sulfite (38 mg, 0.30 mmol) were added and mixed. Then, ethyl acetate (6 mL) was added, and the organic layer was separated, and the aqueous layer was extracted once with a solvent mixture of ethyl acetate (3 mL) and tetrahydrofuran (1 mL). The organic layers were combined and concentrated under reduced pressure to dryness. To the obtained residue, water (8.0 mL) and saturated sodium hydrogencarbonate aqueous solution (2.0 mL) were added and thoroughly mixed. The insoluble matter was filtered off, and to the filtrate, 1M hydrochloric acid (3.0 mL) was added. The precipitated solid was collected by filtration to obtain 2-(4-isothiocyanatophenyl) acetic acid as a colorless solid (0.22 g, yield: 75%, HPLC purity: 95%, HPLC retention time: 3.4 min). LC-MS ES-192 (retention time: 20.5 min, condition 3).

Example 13

4-(4-Isothiocyanatophenyl)butyric acid

Carbon disulfide (0.26 mL, 4.4 mmol) was added to a mixture comprising 4-(4-aminophenyl)butyric acid (0.27 g, 1.5 mmol), tetrahydrofuran (1.0 mL), water (1.0 mL) and triethylamine (0.51 mL, 3.6 mmol), followed by stirring at room temperature for 24 hours. To the obtained reaction mixture, a tetrahydrofuran (1.0 mL) solution of iodine (0.41 g, 1.6 mmol) was dropwise added over a period of 5 minutes at 0° C., followed by stirring at 0° C. for further 1.5 hours. Thereafter, 1M hydrochloric acid (1.5 mL) and sodium sulfite (38 mg, 0.30 mmol) were added and mixed. Then, ethyl acetate (6 mL) was added, and the organic layer was separated, and the aqueous layer was extracted once with a solvent mixture of ethyl acetate (3 mL) and tetrahydrofuran (1 mL). The organic layers were combined and concentrated under reduced pressure to dryness. To the obtained residue, water (8.0 mL) and saturated sodium hydrogencarbonate aqueous solution (2.0 mL) were added and thoroughly mixed. Thereafter, the insoluble matter was filtered off, and to the filtrate, water (8.0 mL) and saturated sodium hydrogencarbonate aqueous solution (2.0 mL) were added and thoroughly mixed, and an insoluble matter was filtered off. The filtrates were combined, and 1M hydrochloric acid (5.0 mL) was added thereto. The precipitated solid was collected by filtration to obtain 4-(4-isothiocyanatophenyl)butyric acid as a colorless solid (0.23 g, yield: 69%, HPLC purity: 97%, HPLC retention time: 3.9 min). LC-MS ES-220(retention time: 4.3 min, condition 2).

Example 14

4-(Isothiocyanatomethyl)benzoic acid

Carbon disulfide (0.26 mL, 4.4 mmol) was added to a mixture comprising 4-(aminomethyl) benzoic acid (0.23 g, 1.5 mmol), tetrahydrofuran (1.0 mL), water (1.0 mL) and triethylamine (0.51 mL, 3.6 mmol), followed by stirring at room temperature for 24 hours. To the obtained reaction mixture, a tetrahydrofuran (1.0 mL) solution of iodine (0.41 g, 1.6 mmol) was dropwise added over a period of 4 minutes at 0° C., followed by stirring at 0° C. for further two hours. Thereafter, 1M hydrochloric acid (1.5 mL) and sodium sulfite (38 mg, 0.30 mmol) were added and mixed. Then, ethyl acetate (6 mL) was added, and the organic layer was separated and the aqueous layer was extracted once with ethyl acetate (3 mL). The organic layers were combined and concentrated under reduced pressure to dryness. To the obtained residue, ethyl acetate (3 mL) was added and thoroughly mixed, and the insoluble matter was filtered off. Then, the filtrate was concentrated under reduced pressure to dryness to obtain 4-(isothiocyanatomethyl)benzoic acid as a cream-colored solid (0.32 g, yield: 109%, HPLC purity: 88%, HPLC retention time: 3.1 min). LC-MS ES-192 (retention time: 3.5 min, condition 2).

Example 15 trans-4-(Isothiocyanatomethyl)cyclohexanecarboxylic acid

Carbon disulfide (0.26 mL, 4.4 mmol) was added to a mixture comprising trans-4-(aminomethyl)cyclohexanecarboxylic acid (0.24 g, 1.5 mmol), tetrahydrofuran (1.0 mL), water (1.0 mL) and triethylamine (0.51 mL, 3.6 mmol), followed by stirring at room temperature for 44 hours. The obtained reaction mixture was dropwise added to a tetrahydrofuran (1.0 mL) solution of iodine (0.41 g, 1.6 mmol) over a period of 5 minutes at 0° C., followed by stirring at 0° C. for further two hours. Thereafter, 1M hydrochloric acid (1.5 mL) was added and mixed. Then, ethyl acetate (6 mL) was added, and the organic layer was separated and concentrated under reduced pressure to dryness. To the obtained residue, a solvent mixture of hexane (3 mL) and ethyl acetate (3 mL) was added and thoroughly mixed, and the insoluble matter was filtered off. Then, the filtrate was concentrated under reduced pressure to dryness to obtain trans-4-(isothiocyanatomethyl) cyclohexanecarboxylic acid as a ocher solid (0.30 g, yield: 101%, and 1H-NMR spectrum showed no distinct by-product). LC-MS ES-198(retention time: 20.3 min, condition 3).

Example 16

6-Isothiocyanatohexanoic acid

Carbon disulfide (0.26 mL, 4.4 mmol) was added to a mixture comprising 6-aminohexanoic acid (0.20 g, 1.5 mmol), tetrahydrofuran (1.0 mL), water (1.0 mL) and triethylamine (0.51 mL, 3.6 mmol), followed by stirring at room temperature for 44 hours. The obtained reaction mixture was dropwise added to a tetrahydrofuran (1.0 mL) solution of iodine (0.41 g, 1.6 mmol) over a period of 5 minutes at 0° C., followed by stirring at 0° C. for further two hours. Thereafter, 1M hydrochloric acid (1.5 mL) and sodium sulfite (38 mg, 0.30 mmol) were added and mixed. Then, ethyl acetate (6 mL) was added, and the organic layer was separated and concentrated under reduced pressure to dryness. To the obtained residue, a solvent mixture of hexane (3 mL) and ethyl acetate (3 mL) was added and thoroughly mixed, and an insoluble matter was filtered off. Then, the filtrate was concentrated under reduced pressure to dryness to obtain 6-isothiocyanatohexanoic acid as an orange oil (0.26 g, yield: 98%, and 1H-NMR spectrum showed no distinct by-product). LC-MS ES-172 (retention time: 19.3 min, condition 3).

Example 17

4-Isothiocyanatobenzoic acid

Carbon disulfide (0.66 mL, 11 mmol) was added to a mixture comprising 4-aminobenzoic acid (0.50 g, 3.6 mmol), acetonitrile (7.7 mL) and triethylamine (1.3 mL, 9.1 mmol.), followed by stirring at room temperature for 16 hours. To the obtained reaction mixture, iodine (1.2 g, 4.8 mmol) was added at 0° C. and stirred for 1.5 hours. Thereafter, 1M hydrochloric acid (9.0 mL), sodium sulfite (0.23 g, 1.8 mmol), water (5.0mL) and ethyl acetate (15 mL) were added and stirred. Then, the solid was collected by filtration and washed with ethyl acetate (10 mL). Obtained crystals were dried under reduced pressure at 50° C. to obtain a crude product (0.42 g) of 4-isothiocyanate benzoic acid as a slightly yellow solid.

Further, the organic layer of the washing solution was separated, and the aqueous layer was extracted with ethyl acetate (30 mL). The organic layers were combined and concentrated under reduced pressure to dryness to obtain a crude product (0.60 g) of brown-colored solid 4-isothiocyanatobenzoic acid.

The obtained crude products of 4-isothiocyanatobenzoic acid were mixed, and 1M hydrochloric acid (3.6 mL) and sodium sulfite (0.092 g, 0.73 mmol) were added and stirred for 0.5 hour. Then, a solid was collected by filtration and washed twice with water (3.0 mL). Obtained crystals were dried under reduced pressure at 50° C. to obtain 4-isothiocyanate benzoic acid as a cream-colored solid (0.61 g, yield: 93%, HPLC purity: 87%).

Example 18

4-Isothiocyanatobenzoic acid

Carbon disulfide (0.67 mL, 11 mmol) was added to a mixture comprising 4-aminobenzoic acid (0.50 g, 3.6 mmol), N,N-dimethylformamide (6.3 mL) and triethylamine (1.3 mL, 9.3 mmol), followed by stirring at room temperature for 4 hours. To the obtained reaction mixture, bromine (0.20 mL, 3.8 mmol) was dropwise added over a period of 20 minutes at 0° C., followed by stirring at 0° C. for further two hours. Thereafter, 1M hydrochloric acid (3.6 mL), sodium sulfite (0.092 g, 0.72 mmol) and water (5.0 mL) were added and mixed. Then, ethyl acetate (15 mL) was added, and the solid was collected by filtration and washed with ethyl acetate (1.0 mL). Obtained crystals were dried under reduced pressure at 50° C. to obtain 4-isothiocyanatobenzoic acid as a slightly yellow solid (0.16 g, yield: 25%, HPLC purity: 94%, HPLC retention time: 3.7 min).

Further, the organic layer of the washing solution was separated, and the aqueous layer was extracted four times ethyl acetate (30 mL). The organic layers were combined and concentrated under reduced pressure to dryness to obtain brown-colored solid 4-isothiocyanate benzoic acid (0.53 g, yield: 81%, HPLC purity: 80%, HPLC retention time: 3.7 min).

The structural formulae of the compounds synthesized in the above Examples 1 to 18 are shown below.

Here, numerals below the respective formulae represent Example numbers.

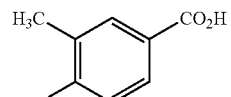

1, 17-18

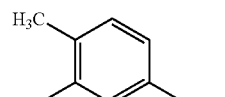

2

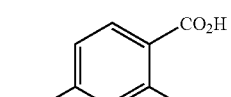

3

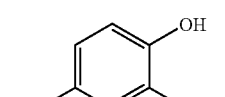

4

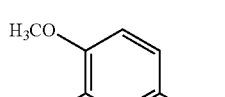

5

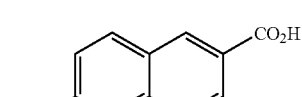

6

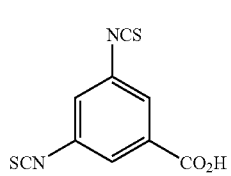

7

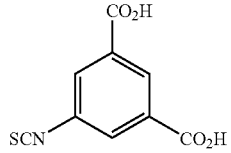

8

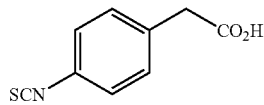

9

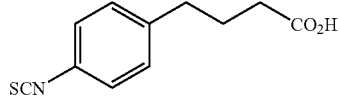

10

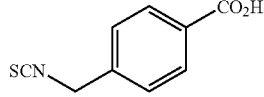

11

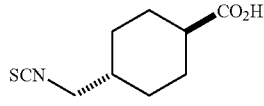

12

13

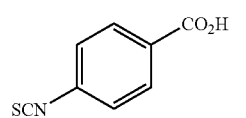

14

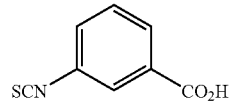

15

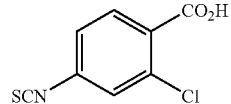

16

INDUSTRIAL APPLICABILITY

An isothiocyanate compound having a carboxyl group(s) obtainable by the method of the present invention is a compound which is industrially very useful as a product or a synthetic intermediate in the field of organic materials or drugs or agricultural chemicals.

The entire disclosures of Japanese Patent Application No. 2008-049369 filed on Feb. 29, 2008 and Japanese Patent Application No. 2008-281184 filed on Oct. 31, 2008 including specifications, claims and summaries are incorporated herein by reference in their entireties.

The invention claimed is:

1. A method for producing an isothiocyanate compound comprising at least one carboxyl group and represented by formula (2):

$$(SCN)_m\text{-A-B-}(CO_2H)_n \qquad (2),$$

wherein m, n, A, and B are, respectively, as defined for formula (1), said method comprising reacting an amino compound comprising at least one carboxyl group and represented by formula (1):

$$(H_2N)_m\text{-A-B-}(CO_2H)_n \qquad (1),$$

wherein:
each of m and n, independent of each other, is 1 or 2;
A is a $C_{6-14}$ aromatic hydrocarbon group or a $C_{1-12}$ saturated hydrocarbon group, wherein said $C_{6-14}$ aromatic hydrocarbon group and $C_{1-12}$ saturated hydrocarbon group are unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a carboxyl group, a $C_{1-6}$ alkylcarbonyl group, and a $C_{1-6}$ alkoxycarbonyl group, and at least one methylene group in said $C_{1-12}$ saturated hydrocarbon group may be replaced by an oxygen atom, a nitrogen atom substituted by a $C_{1-6}$ alkyl group, or a protected nitrogen atom; and
B is a single bond, a second $C_{6-14}$ aromatic hydrocarbon group, or a second $C_{1-12}$ saturated hydrocarbon group, wherein said second $C_{6-14}$ aromatic hydrocarbon group and second $C_{1-12}$ saturated hydrocarbon group are unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a $C_{1-6}$ alkylcarbonyl group, and a $C_{1-6}$ alkoxycarbonyl group, and at least one methylene group in said second $C_{1-12}$ saturated hydrocarbon group may be replaced by an oxygen atom, a nitrogen atom substituted by a $C_{1-6}$ alkyl group, or a protected nitrogen atom,
in a solvent, with carbon disulfide ($CS_2$); and then further reacting with a halogen as a simple substance.

2. The method according to claim 1, wherein:
A is a $C_{6-14}$ aromatic hydrocarbon group unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a $C_{1-6}$ alkylcarbonyl group, and a $C_{1-6}$ alkoxycarbonyl group; and
B is a single bond or a $C_{1-12}$ saturated hydrocarbon group unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a $C_{1-6}$ alkylcarbonyl group, and a $C_{1-6}$ alkoxycarbonyl group, and at least one methylene group in said $C_{1-12}$ saturated hydrocarbon group may be replaced by an oxygen atom, a nitrogen atom substituted by a $C_{1-6}$ alkyl group, or a protected nitrogen atom.

3. The method according to claim 1, wherein A is a $C_{6-14}$ aromatic hydrocarbon group unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a $C_{1-6}$ alkylcarbonyl group, and a $C_{1-6}$ alkoxycarbonyl group, and B is a single bond or a $C_{1-6}$ alkyl group.

4. The method according to claim 3, wherein A is a $C_{6-14}$ aromatic hydrocarbon group unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a $C_{1-6}$ alkylcarbonyl group, and a $C_{1-6}$ alkoxycarbonyl group, and B is a single bond.

5. The method according to claim 4, wherein A is a $C_{6-14}$ aromatic hydrocarbon group unsubstituted or substituted by at least one selected from the group consisting of a halogen atom, a $C_{1-6}$ alkyl group, a hydroxyl group, and a $C_{1-6}$ alkoxy group.

6. The method according to claim 1, wherein:
A is a $C_{1-12}$ saturated hydrocarbon group unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a carboxyl group, a $C_{1-6}$ alkylcarbonyl group, and a $C_{1-6}$ alkoxycarbonyl group, and at least one methylene group in said $C_{1-12}$ saturated hydrocarbon group may be replaced by an oxygen atom, a nitrogen atom substituted by a $C_{1-6}$ alkyl group, or a protected nitrogen atom; and
B is a single bond or a $C_{6-14}$ aromatic hydrocarbon group unsubstituted or substituted by at least one selected from the group consisting of a halogen atom, a nitro group, a cyano group, a $C_{1-6}$ alkyl group, a hydroxyl group, a protected hydroxyl group, a $C_{1-6}$ alkoxy group, a di $C_{1-6}$ alkylamino group, a protected amino group, a protected mono $C_{1-6}$ alkylamino group, a $C_{1-6}$ alkylcarbonyl group, and a $C_{1-6}$ alkoxycarbonyl group.

7. The method according to claim 6, wherein A is a $C_{1-12}$ saturated hydrocarbon group, and B is a single bond or a $C_{6-14}$ aromatic hydrocarbon group unsubstituted or substituted by at least one selected from the group consisting of a halogen atom, a $C_{1-6}$ alkyl group, a hydroxyl group, and a $C_{1-6}$ alkoxy group.

8. The method according to claim 7, wherein A is a $C_{1-12}$ saturated hydrocarbon group, and B is a single bond or a $C_{6-14}$ aromatic hydrocarbon group.

9. The method according to claim 8, wherein A is a $C_{1-12}$ saturated hydrocarbon group, and B is a single bond.

10. The method according to claim 8, wherein A is a $C_{1-6}$ saturated hydrocarbon group, and B is a phenyl group.

11. The method according to claim 1, wherein m is 1.

12. The method according to claim 1, wherein n is 1.

13. The method according to claim 1, wherein m is 2.

14. The method according to claim 1, wherein n is 2.

15. The method according to claim 1, wherein the reacting of the amino compound comprising at least one carboxyl group with carbon disulfide is carried out in the presence of a base.

16. The method according to claim 15, wherein the base is an organic amine or an inorganic base.

17. The method according to claim 1, wherein the halogen as a simple substance is iodine.

* * * * *